(12) United States Patent
Haskell et al.

(10) Patent No.: US 7,580,831 B2
(45) Date of Patent: Aug. 25, 2009

(54) DYNAMIC DICTIONARY AND TERM REPOSITORY SYSTEM

(75) Inventors: Robert Emmons Haskell, Chester Springs, PA (US); John Andrew Heil, Malvern, PA (US); James Cassidy, Phoenixville, PA (US)

(73) Assignee: Siemens Medical Solutions Health Services Corporation, Malvern, PA (US)

( * ) Notice: Subject to any disclaimer, the term of this patent is extended or adjusted under 35 U.S.C. 154(b) by 918 days.

(21) Appl. No.: 10/379,880

(22) Filed: Mar. 5, 2003

(65) Prior Publication Data

US 2003/0233251 A1    Dec. 18, 2003

Related U.S. Application Data

(60) Provisional application No. 60/361,754, filed on Mar. 5, 2002.

(51) Int. Cl.
*G06F 17/27* (2006.01)
*G06F 17/21* (2006.01)

(52) U.S. Cl. .............................. 704/10; 704/9
(58) Field of Classification Search ............... 704/9, 704/10
See application file for complete search history.

(56) References Cited

U.S. PATENT DOCUMENTS

| | | | | |
|---|---|---|---|---|
| 5,251,316 A | * | 10/1993 | Anick et al. ............... | 707/101 |
| 5,560,005 A | | 9/1996 | Hoover et al. .............. | 395/600 |
| 5,642,518 A | * | 6/1997 | Kiyama et al. .............. | 704/7 |
| 5,652,898 A | * | 7/1997 | Kaji ......................... | 704/10 |
| 5,664,109 A | * | 9/1997 | Johnson et al. ............ | 705/2 |
| 5,809,471 A | * | 9/1998 | Brodsky .................... | 704/275 |
| 5,809,476 A | | 9/1998 | Ryan ........................ | 705/2 |
| 5,819,263 A | | 10/1998 | Bromley et al. | |
| 5,832,450 A | | 11/1998 | Myers et al. .............. | 705/3 |

(Continued)

FOREIGN PATENT DOCUMENTS

WO    WO 96/41288    12/1996

(Continued)

OTHER PUBLICATIONS

Jian-Yun Nie, Marie-Louise Hannan, Wanying Jin, "Unknown Word Detection and Segmentation of Chinese Using Statistical and Heuristic Knowledge", 1995, Communications of the Chinese and Oriental Languages Information Processing Society.*

(Continued)

*Primary Examiner*—Richemond Dorvil
*Assistant Examiner*—Eric Yen
(74) *Attorney, Agent, or Firm*—Alexander J. Burke

(57) ABSTRACT

A dictionary system provides a term repository supporting the operation of an enterprise, which dynamically updates its content in response to system use. An input processor acquires transaction message data in at least one of a plurality of different data formats. A data processor parses the acquired transaction message data to extract a term from the message data. The processor then compares the extracted term to terms in a first term repository. The first term repository is updated to include the extracted term if the extracted term is absent from said first term repository. A communication processor intermittently processes the content of said first term repository to be suitable for communication to a second term repository.

24 Claims, 1 Drawing Sheet

System

U.S. PATENT DOCUMENTS

| | | | |
|---|---|---|---|
| 5,867,821 | A | 2/1999 | Ballantyne et al. |
| 5,915,240 | A * | 6/1999 | Karpf .............................. 705/2 |
| 5,924,074 | A | 7/1999 | Evans |
| 5,970,492 | A * | 10/1999 | Nielsen ........................ 707/10 |
| 5,991,728 | A | 11/1999 | DeBusk et al. .................. 705/2 |
| 6,018,713 | A | 1/2000 | Coli et al. |
| 6,055,494 | A | 4/2000 | Friedman ........................ 704/9 |
| 6,112,183 | A | 8/2000 | Swanson et al. |
| 6,163,781 | A | 12/2000 | Wess, Jr. ...................... 707/103 |
| 6,173,253 | B1 * | 1/2001 | Abe et al. ...................... 704/10 |
| 6,260,021 | B1 | 7/2001 | Wong et al. |
| 6,263,330 | B1 | 7/2001 | Bessette |
| 6,282,508 | B1 * | 8/2001 | Kimura et al. ................. 704/10 |
| 6,311,163 | B1 | 10/2001 | Sheehan et al. |
| 6,311,192 | B1 | 10/2001 | Rosenthal et al. ........... 707/200 |
| 6,345,245 | B1 * | 2/2002 | Sugiyama et al. ............. 704/10 |
| 6,347,329 | B1 | 2/2002 | Evans |
| 6,785,869 | B1 * | 8/2004 | Berstis ........................ 715/532 |
| 6,789,057 | B1 * | 9/2004 | Morimoto et al. ............... 704/2 |
| 2001/0027403 | A1 | 10/2001 | Peterson et al. |
| 2001/0041992 | A1 | 11/2001 | Lewis et al. .................... 705/3 |
| 2001/0051879 | A1 | 12/2001 | Johnson et al. ................. 705/2 |
| 2001/0051880 | A1 | 12/2001 | Schurenberg et al. .......... 705/3 |
| 2001/0051889 | A1 | 12/2001 | Haney |
| 2002/0007284 | A1 | 1/2002 | Schurenberg et al. .......... 705/2 |
| 2002/0007287 | A1 | 1/2002 | Straube et al. |
| 2002/0023067 | A1 | 2/2002 | Garland et al. |
| 2002/0046346 | A1 | 4/2002 | Evans |
| 2002/0055917 | A1 | 5/2002 | Muraca |
| 2002/0082868 | A1 | 6/2002 | Pories et al. .................... 705/3 |
| 2003/0233252 | A1 | 12/2003 | Haskell |

FOREIGN PATENT DOCUMENTS

| | | |
|---|---|---|
| WO | WO 97/32271 | 9/1997 |

OTHER PUBLICATIONS

Y. Liu and Y. Satomura: "Building a Controlled Health Vocabulary in Japanese" *Methods of Information in Medicine*, 40:4 2001, pp. 307-315 XP008026570 Abstract.

International Search Report.

SMS "Common Vocabulary Engine" Jul. 1999.

Soarian knows System Architecture Siemens Medical.

Siemens "Siemens Reference Architecture Overview" Aug. 2003.

Love. Brian J. "Un Edifact—an EDI Standard for health Care," *Progress in Standardization in Health Care Informatics*, G.J.E. De Moor et al. (Eds.) 1993 pp. 156-161.

De Moor. Georges J.E., "Towards a meta-syntax for Medical edi," *International Journal of Bio-Medical Computing*, vol. 34 No. ¼, pp. 319-330 (1994).

Kinkhorst, O.M., at al., "From Medical Record to Patient Record Through Electronic Data Interchange (EDI)," *International Journal of Bio-Medical Computing*, Elsevier Science Publishers, vol. 41 No. 1 Jul. 1996 pp. 151-155.

U.S. Appl. No. 10/252,972, filed Sep. 23, 2002, Robert Emmons Haskell et al.

Michael A. Hogarth et al., Terminology Query Language: A Server Interface for Concept-Oriented Terminology Systems. Abstract, 2000.

Kim Batch, Who needs a standard medical terminology . . . Enterprise Architect Center for Biomedical Informatics University of Pittsburgh.

Apelon http://www.apelon.com/products/products.htm, May 22, 2002.

* cited by examiner

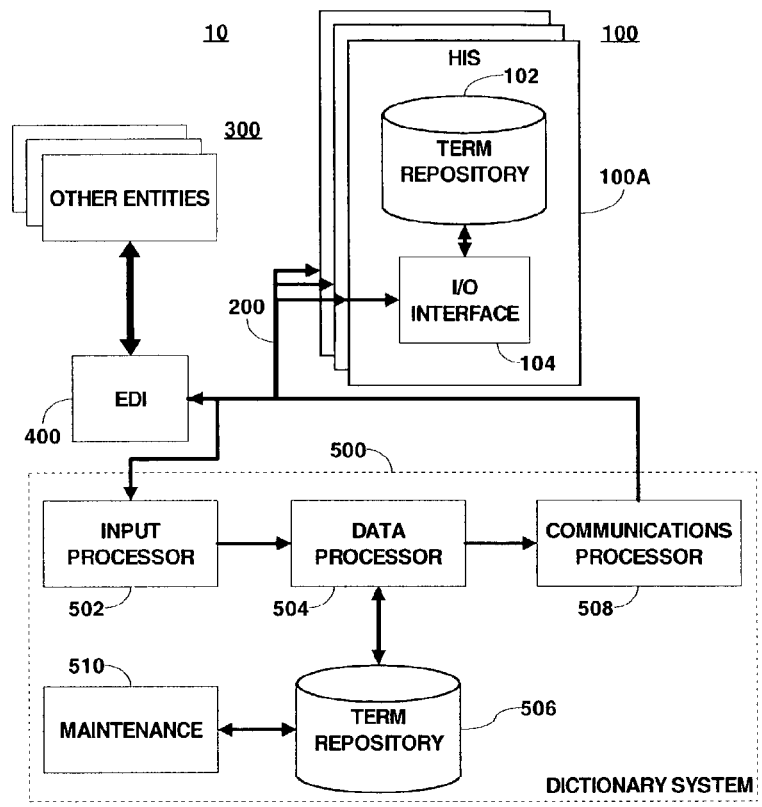
Fig. 1 - System
Fig. 2 – Term Repository

DYNAMIC DICTIONARY AND TERM REPOSITORY SYSTEM

This application is a non-provisional application of provisional application No. 60/361,754 by R. E. Haskell et al. filed Mar. 5, 2002.

FIELD OF THE INVENTION

The present invention relates to a dictionary and term repository system which may be used to support a healthcare enterprise.

BACKGROUND OF THE INVENTION

A healthcare enterprise is made up of one or more related healthcare facilities and may also be associated with other entities not included in the healthcare enterprise. Healthcare information systems store information related to patients of the healthcare enterprise. The patient information is exchanged over a communications network interconnecting the various facilities in the healthcare enterprise. Some such information is easily handled by computing systems: for example, demographic information such as patient name, age, sex, race, address, etc.; and fiscal data such as coding, billing, collections, appeals, etc. However, the most critical part of the patient record is the medical information: for example, clinical information such as symptoms, signs, side effects, complications, etc.; and outcomes such as performance, effectiveness, efficiency, etc. To be useful, these records need to be searchable on the medical terms in them, either for the particular patient (e.g., to apply best practice rules) or over a population of patients (e.g., to develop best practice rules).

However, one problem is that in medical records different terms may be used by different facilities and/or doctors for the same or similar concepts. For example, the terms: "heart is enlarged", "enlarged heart", "heart shows enlargement", and "cardiac enlargement" have the same meaning, and may be translated to a canonical or regular term: "enlarged heart". Similarly, the same term may have different meanings to different facilities within the healthcare enterprise. For example, "cystic disease" has one meaning in X-ray diagnosis and a different meaning in mammography.

In order to provide complete and accurate results when searching for records related to a medical concept, all terms which may be used to represent that concept need to be found in the search. To facilitate this function, each healthcare information system within the healthcare enterprise maintains a lexicon or dictionary which contains a repository of medical terms (i.e. words or phrases) which may be used in medical transactions in that facility. Searches may then be performed by looking up the regular term associated with each search term, analyzing the medical records to identify the regular terms associated with the terms used in the medical record, and performing the search using the regular terms, all in a known manner.

US Patent publication 2002/0082868, published Jun. 27, 2002 for Pories et al., relates to a system for creating an electronic medical record. A general illness for a patient is first identified and supplied to the system via an input device. In response, a series of screen images are presented to the doctor displaying a plurality of terms, which had been pre-entered into a lexicon, related to the illness. The doctor selects from among the displayed list of terms to describe the results of his examination. In response to the doctor's selections, other screen images with other lists of terms, related to those previously selected, may be displayed, and the doctor may select from among those displayed, until the required level of detail is reached. All of the selected terms are then processed to automatically generate structured medical information for the medical record. A term may be manually added to the lexicon, possibly after the approval of a medical director or other person of authority. For example, if a desired term is not in the lexicon, a doctor may request that it be added to the lexicon. In addition, medical texts may be scanned and parsed, and terms found in the texts automatically added to the lexicon. Also, third party sources, such as hospital, insurance, and/or federal agency databases, may be scanned and parsed to extract relevant terms and the extracted terms added to the lexicon. Further automatic processes may be performed to delete terms which have fallen into disuse.

U.S. Pat. No. 6,055,494, issued Apr. 25, 2000 to Friedman, discloses a system for parsing natural language medical records. A natural language medical record is parsed and its terms compared to entries in the database to assign a canonical term for any natural language expression corresponding to that canonical term. A database is used to hold information necessary to perform the parse. The regular terms resulting from the parsing of the natural language medical record are then further processed. For example, they may be stored in a database record so that all such medical records may be searched using the regular terms.

U.S. Pat. No. 5,809,476, issued Sep. 15, 1998 to Ryan, discloses a system for generating coded data from natural language medical records. Each term in the medical record, and relationships between terms, are analyzed to generate a compressed symbolic representation of the original information. The system provides for correction and/or supplement of the original information. This coded information may later be interrogated.

By parsing and/or coding medical records to identify regular or canonical terms for the medical terms being recorded, the future searching of such records is facilitated, best practice rules may be defined using these terms, and more meaningful statistical analyses of the medical records may be performed.

In Pories et al. only those terms in the lexicon are displayed and made available for a doctor to include in his medical record. In the other systems, only the terms in the lexicon are recognized and coded. Thus, all of the above mentioned systems require a populated database or lexicon to operate. However, the population of such a lexicon can be a time consuming and lengthy process, which may unduly restrict doctors when delivering health care and creating their own medical records. Also, even if automatically created from prior lexicons or from literature, there is no is no assurance that terms collected are relevant to the facility or doctor.

In Pories et al., a doctor may request a term be added to the lexicon. But the update is made manually, possibly only upon approval of a medical director. This system may also automatically delete terms which have not been used for some predetermined time. Neither Friedman nor Ryan disclose dynamically updating the lexicon in response to use of the system.

The requirement for a full lexicon means that such systems require an installation of such a lexicon before they may be used. Installation of a full lexicon may be accomplished in two ways: by moving a lexicon from one or more remote locations to the current health information system; and/or by manually entering the desired terms into the lexicon. The former requires that programs be written which can read the pre-existing lexicon in its format, and write the new lexicon in its, possibly different, format. The development of this program, its testing and execution require a substantial amount of time, and risks carrying over old, unused terms from the old lexicon into the new one. The latter takes even more time, and has a very high probability of the new lexicon having errors, omissions and inaccuracies.

A system which does not require a full lexicon to begin operation, provides a means to rapidly and accurately build a significant portion thereof, and which provides for full and accurate searching of medical records is desirable.

BRIEF SUMMARY OF THE INVENTION

In accordance with principles of the present invention a dictionary system provides a term repository supporting the operation of an enterprise, which dynamically updates its content in response to system use. An input processor acquires transaction message data in at least one of a plurality of different data formats. A data processor parses the acquired transaction message data to extract a term from the message data. The processor then compares the extracted term to terms in a first term repository. The first term repository is updated to include the extracted term if the extracted term is absent from said first term repository. A communication processor intermittently processes the content of said first term repository to be suitable for communication to a second term repository. This second term repository represents the operational term repository for a health information system of one of the healthcare enterprise facilities.

BRIEF DESCRIPTION OF THE DRAWING

In the drawing:

FIG. 1 is a block diagram of a portion of a healthcare enterprise data processing system including a data dictionary system according to principles of the present invention; and FIG. 2 is a data diagram illustrating a portion of the contents of a term repository table in the data dictionary system illustrated in FIG. 1.

DETAILED DESCRIPTION OF THE INVENTION

FIG. 1 is a block diagram of a portion of a healthcare enterprise data processing system including a data dictionary system according to principles of the present invention. Only those elements necessary to describe a data dictionary according to principles of the present invention are illustrated in FIG. 1. One skilled in the art will understand what other elements are necessary for a healthcare enterprise data processing system, how to specify, design, and implement those elements, and how to interconnect those other elements with the illustrated elements to form a working data processing system.

In FIG. 1, a healthcare enterprise includes a plurality of healthcare information systems (HISs) 100, each providing data processing services for one or more operational facilities in the healthcare enterprise. For example, a healthcare enterprise may include a healthcare enterprise laboratory, a healthcare enterprise pharmacy, healthcare enterprise radiology department, a healthcare enterprise modality department, a healthcare enterprise administration operation, a healthcare enterprise orders or results management operation, and other such operations.

These HISs are interconnected using a network connection 200, including any of a wireless network, wired network (e.g. Ethernet), or any other form of computer interconnection structure. Each of the HISs 100 includes an input/output (I/O) processor 104 for receiving data from and transmitting data to the network connection 200. At least one of the HISs 100 also includes a term repository 102, containing data representing terms which describe the vocabulary of the users of that HIS and may be used to enter information, validate information, identify courses of treatment, and implement searches of the data records contained in that HIS 100, in a manner described above. This dictionary may also contain other information associated with each term, such as a canonical or regular term, other synonyms if they exist, a count of the frequency of occurrence of the term (described in more detail below), a definition, etc. It is also possible for the dictionary to contain information representing the relationship of a term to other terms within a hierarchy of terms, such as might be used to describe the results of a battery of tests such as the complete blood count (CBC) laboratory test.

The network connection 200 is also coupled to an electronic data interchange (EDI) circuit 400. The EDI 400 provides a bridge between the enterprise network connection 200 and other entities 300 inside or outside the enterprise. For example, these entities 300 may include doctors' offices, laboratories, pharmaceutical companies, payers, etc.

The network connection 200 is also coupled to a dictionary system 500 in accordance with principles of the present invention. An input terminal of an input processor 502 is coupled to, and receives data from the network connection 200. An output terminal of the input processor 502 is coupled to an input terminal of a data processor 504. An output terminal of the data processor 504 is coupled to an input terminal of a communications processor 508. An output terminal of the communications processor 508 is coupled to and transmits data to the network connection 200. A term repository 506 is bidirectionally coupled to the data processor 504. A maintenance processor 510 is bidirectionally coupled to the term repository 506.

In operation, the various HISs 100, the EDI 400 and the data dictionary system 500 communicate by sending transaction messages over the network connection 200. Such transaction messages contain data which may include: (a) a communication involving a healthcare enterprise laboratory, (b) a communication involving a healthcare enterprise pharmacy, (c) a communication involving a healthcare enterprise radiology department, (d) a communication involving a healthcare enterprise modality department, (e) a communication involving a healthcare enterprise administration operation (f) a communication involving a healthcare enterprise orders or results management operation; and/or any other data to be communicated between one facility within the healthcare enterprise and other facility within or without the enterprise.

These transaction messages are sent from a source (e.g. one HIS 100) to a destination (e.g. another HIS 100). At the destination, the incoming transaction message is queued for further processing. The transaction messages in the queue are then processed in their turn. To enhance reliability, the data fields in each transaction message in the queue are analyzed and processed in a reversible manner until it is clear that the transaction message is complete and accurate. This processing may include review by a human user. If the transaction message is complete and accurate, then the transaction message is 'posted', meaning that any changes specified by the data fields in the transaction message are made at the destination, and the transaction message is removed from the queue. In this manner, if it is found that a transaction message is defective in any manner, e.g. by missing data, by containing corrupt data, or by including conflicting or nonsensical data, etc., no 'posting' is made and therefore no incorrect changes are made in the destination HIS. Further, the source HIS may be informed of the problem.

In a healthcare enterprise data processing system, such as is illustrated in FIG. 1, different HISs may be supplied by different vendors and therefore may communicate transaction messages containing different data using different data formats, called protocols, for the transactions. There are several known protocols for forming transaction messages: Health Level Seven (HL7), Extensible Markup Language (XML), Digital Imaging and Communications in Medicine (DICOM), or any other electronic data interchange (EDI) protocol recognized by the American National Standards Institute's (ANSI) Accredited Standards Committee (ASC) X12. Regardless of the protocol, each transaction message includes several data fields, representing inter alia: the transaction message source location, the transaction message protocol, and the type of computer system at the transaction message source location. In some cases, for example for those transmitting medical records, the transaction message further includes data fields representing coded medical data and/or the text of the medical record.

In general, the dictionary system 500, according to principles of the present invention, monitors the transaction message stream that flows through the network connection 200 connecting the multiple HISs 100 in the healthcare enterprise system 100 and Other Entities 300, and stores new terms (including medical codes) found in those transactions in a structured repository 506 of such terms. In a similar manner to the facility term repository 102 discussed above, the term repository 506 in the dictionary system 500 may also contain other information associated with each term, such as a canonical or regular term, other synonyms if they exist, a count of the frequency of use of the term, a definition, etc. It is also possible for the term repository 506 to contain information representing the relationship of a term to other terms within a hierarchy of terms, such as might be used to describe the results of a battery of tests such as the complete blood count (CBC) laboratory test, as described in more detail below.

The respective transaction message data fields representing coded medical data and/or texts of medical records are parsed to identify and extract codes or terms. New terms are added to the repository and counts are maintained of repeated terms. Utilities are provided to manage the repository, including viewing and maintaining its content (e.g., display the most frequently occurring terms, delete terms, reset counts, generate updates for the HIS term repository 102). As preparation for installing a new HIS system containing a new term repository 102, the central tern repository 506 can be turned on early to collect a baseline set of terms, which can be subsequently refined to reflect new terminology requirements of the new HIS system. No complex installation is required because the new dictionary builds itself as transaction messages are processed.

More specifically, the input processor 502 acquires transaction messages from the network connection 200 in at least one of the protocols, described above, in which the transaction messages are formatted. Preferably, however, the input processor 502 may properly acquire transaction messages in any of the protocols used in the system. To do this, the input processor 502 needs to know what protocol is being used to format the transaction message. As described above, each transaction message includes a data field representing the protocol of that transaction message. The input processor 502 extracts the value in that data field and in response conditions its own processing to properly acquire the remainder of the transaction message data.

The data processor 504 further processes the acquired transaction messages to update the term repository 506, as described generally above. First, the acquired transaction message data, and in particular the data field representing the medical data, is parsed to extract the terms in it. Predetermined templates of transaction messages in the different possible protocols are developed and used to provide some basic positional information to drive the message parsing function. This satisfies the need to accommodate in a general way the different standard message protocols of the source systems. Each such extracted term may be a word, a code, a symbol, a label, text, a text expression, a designation, a string of characters, or any other such grouping of symbols which, taken as a whole, represents a medical concept. Second, each term which is thus extracted is compared to the terms currently in the term repository 506. Third, the term repository 506 is updated. If the term is not in the term repository 506, it is added. When the term is added to the term repository 506, other data fields in the term repository 506 are also initialized with data related to the term and/or the transaction message containing the term. Optionally, if the term is in the term repository, then a data field in the term repository 506 containing a usage count is incremented by one. This count will increase indefinitely until reset at some point in time by the user of the maintenance facility 510, such as when distributing an update to the facility term repositories or when an analysis of new usage counts is desired. When a term is initially added to the term repository 506, the usage count data field is initialized to one.

FIG. 2 is a data diagram illustrating a portion of the contents of a term repository table 600 in the data dictionary system 500 illustrated in FIG. 1. More specifically, key data fields, used for indexing the contents of the table 600, contain a source identification (ID) code representing the transaction message source and a term identification (ID) code representing the term itself, illustrated as the leftmost two columns in FIG. 2. Each facility in the healthcare enterprise 100, and potentially each facility across all healthcare enterprises and other entities from which data might be received, for example, external facilities, and government and/or insurance industry databases, has associated with it an identification code. It is also possible for other sources of terms, such as medical texts, to be assigned an identification code.

Including a source ID code as a key data field is needed to identify and maintain separately those identical terms that might have different meanings in different HIS facilities, as described above. Consolidation rules may be applied later by the maintenance processor 510 to merge identical terms with the same meaning, and to separate terms with different meanings. One skilled in the art would understand how to generate consolidation rules which may be applied later within the maintenance processor 510.

As described above, each transaction message includes a data field representing the identity of the source of that transaction message. When a transaction message is parsed by the data processor 504, each term in that transaction message is associated with the ID code of the source. In addition, when a term is extracted from the transaction message, the data processor 504 associates a term identification code with that term. If this term is already in the term repository table 600, the term ID is already in the table. If the term is not already in the term repository table 600, the data processor 504 associates a unique term ID with that new term. As described above, if the newly parsed term is not already in the term repository table 600, a new record is added with the source ID and term ID in the key data fields.

Further data fields in the term repository table 600 are illustrated from left to right for containing the full name of the source system, the extracted term in text form, the date and time the last transaction message was received, and the status of the term. These fields are initialized when the term is first added to the table 600. Also, another data field includes the usage count, described in detail above. Other fields (not shown) may also be provided to contain supporting detail for the term, the relationship to other terms, the date and time the term entry was first created, and any other information related to the term. Each term extracted from the transaction messages has a record in the term repository table 600.

Referring again to FIG. 1, the maintenance processor 510 provides a means for maintaining the term repository 506. The maintenance processor 510 accesses the contents of the term repository 506 to allow a user to view the terms and related data, manually add a term, manually delete a term, manually edit a term, and reset or otherwise adjust usage frequency counts. The maintenance processor 510 may also generate reports related to the accumulated terms, all in a known manner. The maintenance processor 510 also can evaluate the date/time field in the term repository table 600 to identify terms that haven't been used in transaction messages in a predetermined time interval. Any such identified term may be inactivated by deleting the record from the table 600, marking the term status field as INACTIVE, moving the record to a separate table (not shown) which holds inactive terms, and/or any other suitable technique. The maintenance processor 510 also allows a user to initiate update of a facility HIS 100 term repository 102 in a manner described in more detail below.

As described above, respective HISs 100 in the operational facilities in the healthcare enterprise each include their own term repository 102 to contain the vocabulary which is relevant to that facility. The facility term repositories 102 are initialized and/or updated using the terms accumulated in the dictionary system 500 and possibly from other sources specific to the facility HIS. The communications processor 508 conditions the data processor 504 to process the content of the dictionary 500 term repository 506 to be suitable to communicate to the term repository 102 in a facility HIS 100. More specifically, the data processor 504 is conditioned to select those terms having a source ID associated with the facility (or possibly other facilities or sources as desired and appropriate) and/or with other record attributes that match predetermined rules, such as a time period for new terms added. The selected terms and other associated data fields are then mapped and arranged as required by the facility HIS 100 term repository 102. These data fields are then communicated over the network connection 200 to the facility HIS 100 via a file and/or one or more transaction messages using the protocol required by the facility HIS 100. Upon receiving these transaction messages, the facility HIS 100 updates its term repository 102. The updating of the facility HIS 100 term repository 102 may be initiated by a user command issued from the maintenance processor 510, as described above. Alternatively, an update may be initiated by a command issued automatically in response to any desired criterion. For example, an update may be initiated in response to either a predetermined interval of time since the last update, the accumulation of a predetermined number of terms since the last update, or identification of terms having usage counts exceeding a predetermined threshold. The facility term repository 102 may also be updated in an incremental manner by selecting only terms in the central term repository 506 which were added after a selected date (e.g. the date of the last update), and updating the facility term repository 102 with those terms.

It is also important to have some form of filtering on this upload process, especially if applying new content to an existing facility-specific term repository. Therefore, the update may be based on more complicated criteria. A user may perform a query on the central term repository 506 to identify a set of terms matching desired criteria, such as only new terms acquired within a particular time period, or criteria based on attributes of the terms themselves such as only terms acquired from a particular source, or only terms of a particular status. The facility term repository 102 is updated with only these terms. Identical terms from different sources having the same canonical meaning may be consolidated, as described above, and those consolidated terms sent to the facility term repository 102. Alternatively, a selected type of term, for example laboratory terms, may be extracted and only those terms sent to the facility term repository 102. Further, as illustrated in FIG. 2, the source of the term is included in the database. As described above, the source may be a medical text, or a government or insurance industry database. Terms from these sources may need to be supplied to the facility term repository 102 as soon as practical after they are identified. In all of these examples, the database 600 in the term repository 506 is queried to identify desired terms and the selected terms sent to the facility term repository 102. One skilled in the art will understand that the above described methods are simply examples, and that any such method may be used to identify sets of terms and to initiate updating of the facility term repository 102 with these terms.

By accumulating terms in a central term repository (506) by monitoring transaction messages passing through the network connection (200), as described above, terms in a facility term repository (102) may be initially installed without requiring a full installation process. Instead, installation of terms occurs as those terms are used. Alternatively transaction streams may be monitored by a central term repository 506 while waiting for a new system to be delivered and the facility term repository 102 may be updated from the central term repository 506 when finally installed. This obviates the time and expense inherent in writing and testing software to transfer terms from pre-existing term repositories or medical texts, and eliminates the unreliability inherent in manual entry of terms into the new term repository. Instead, terms are accumulated rapidly and accurately, as the terms are used, and therefore needed. New terms are identified and integrated on an ongoing basis.

This invention has been described above in an embodiment of a healthcare enterprise including multiple HISs in corresponding healthcare facilities within the enterprise. However, one skilled in the art will understand that this invention may also serve as a generic extension to a single HIS, or as a general health industry data dictionary used, for example, for regional health surveillance or any other such purpose. In addition, there is nothing in this technique which is specific to healthcare and HISs. Any vocabulary term repository may be created and maintained by monitoring transaction streams carrying transactions in which terms are included, according to the invention, provided there is a standard within the data streams which will permit the necessary parsing and identification functions.

What is claimed is:

1. A healthcare dictionary system providing a term repository accessible for use in supporting the operation of a healthcare enterprise, comprising:

an input processor for acquiring healthcare transaction message data including data for communication from a first healthcare facility to at least a second different healthcare facility in at least one of a plurality of different communication protocol data formats and being communicated between different facilities of a healthcare enterprise;

a data processor for,
parsing said acquired transaction message data to identify a communication protocol data format of said transaction message and extracting a term from said acquired transaction message data,
comparing said extracted term to terms in a first term repository, said first term repository including at least one of,
(a) definitions indicating meaning of a plurality of healthcare terms used by a particular healthcare facility and
(b) synonyms of a plurality of healthcare terms used by a particular healthcare facility and
updating said first term repository to include said extracted term in response to a determination, said extracted term is absent from said first term repository; and
a communication processor for intermittently processing content of said first term repository to be suitable for communication to a second term repository including definitions of a plurality of healthcare terms used by a different healthcare facility.

2. The system according to claim 1 wherein the data processor further updates the first term repository to increment a usage count for the extracted term in the first term repository in response to a determination that said extracted term is present in the first term repository.

3. The system according to claim 2 further comprising a maintenance processor, coupled to the first term repository, for maintaining the contents of the first term repository and wherein
said data processor is conditioned in response to said identified data format, selected from said plurality of different data formats, to extract said term from said acquired transaction message data.

4. The system according to claim 3 wherein the maintenance processor allows a user to reset the usage count for a term in the first term repository.

5. The system according to claim 1 further comprising a maintenance processor, coupled to the first term repository, for maintaining the contents of the first term repository.

6. The system according to claim 5 wherein the maintenance processor allows a user to do one or more of: (a) view a term in the first term repository, (b) add a term to the first term repository, (c) delete a term from the first term repository, (d) edit a term in the first term repository, and (e) generate a report related to the terms in the first term repository.

7. A system according to claim 1, wherein said data processor further extracts at least one of, (a) transaction message source identification information, (b) transaction message protocol identification information and (c) transaction message source computer system identification information.

8. A system according to claim 1, wherein said transaction message data comprises at least one of, (a) a communication involving a healthcare enterprise laboratory, (b) a communication involving a healthcare enterprise pharmacy, (c) a communication involving a healthcare enterprise radiology department, (d) a communication involving a healthcare enterprise modality department, (e) a communication involving a healthcare enterprise administration operation and (f) a communication involving a healthcare enterprise orders or results management operation.

9. A system according to claim 1, wherein said first term repository is used to update a plurality of different health care information system term repositories including said second term repository.

10. The system according to claim 9 further comprising a maintenance processor, coupled to the first term repository, for initiating an update of said second term repository.

11. The system according to claim 10 wherein the update is initiated in response to a user command.

12. The system according to claim 10 wherein the update is initiated automatically in response to satisfaction of a predetermined criterion.

13. The system according to claim 12 wherein the predetermined criterion relates to dates respective terms were included in the first term repository.

14. A system according to claim 13, wherein said data processor processes said extracted term to be compatible with said first term repository by storing said term in said first term repository together with at least one of, (a) a term identifier code created by said data processor and (b) an organization identifier code associated with a source system of said extracted term.

15. The system according to claim 12 wherein the predetermined criterion relates to the number of terms included in the first term repository.

16. The system according to claim 12 wherein the predetermined criterion relates to attributes of terms included in the first term repository.

17. A system according to claim 1, wherein said data processor processes said extracted term to be compatible with said first term repository by storing said term in said first term repository together with at least one of, (a) date or time said term is received, (b) a source system identifier, (c) a term status and (d) an updated indication of a number of times said term has been detected.

18. A system according to claim 1, wherein said data processor processes said extracted term to be compatible with said first term repository by storing said term in said first term repository together with at least one of, (a) a term identifier code created by said data processor and (b) an organization identifier code associated with a source system of said extracted term.

19. The system of claim 18 wherein:
the enterprise is a healthcare enterprise and the dictionary system is a healthcare dictionary system; and
the input processor acquires healthcare transaction message data as the transaction message data.

20. A system according to claim 1, wherein said extracted term comprises at least one of, (a) a word, (b) a code, (c) a symbol, (d) a label, (e) text, (t) a text expression, (g) a designation, and (h) a string of characters, derivable from transaction message data communicated in support of healthcare enterprise operation.

21. A healthcare dictionary system, comprising:
an input processor for acquiring healthcare transaction message data in at least one of a plurality of different data formats and being communicated between different facilities of a healthcare enterprise;
a data processor for,
parsing said acquired transaction message data to identify a data format of said transaction message from said plurality of different data formats,
conditioning said data processor to process data in said identified data format,
extracting a term from said acquired transaction message data in said identified data format,
comparing said extracted term to terms in a first term repository, said first term repository including definitions indicating meaning of a plurality of healthcare terms used by a particular healthcare facility and updating said first term repository to include said extracted term in response to a determination, said extracted term is absent from said first term repository; and a communication processor for processing content of said first term repository to be suitable for communication to at least one of a plurality of different health care information system term repositories including definitions of a plurality of healthcare terms used by said at least one of a plurality of different healthcare information systems and update of said at least one health care information system term repository, in response to a received command.

22. A healthcare dictionary system, comprising:

an input processor for acquiring healthcare transaction message data in at least one of a plurality of different data formats and being communicated between different facilities of a healthcare enterprise;

a data processor for, parsing said acquired transaction message data including data for communication from a first healthcare facility to at least a second different to identify a communication protocol data format of said transaction message from said plurality of different communication protocol data formats and extracting a term from said acquired transaction message data in said identified data format, comparing said extracted term to terms in a first term repository associating a term identifier code with said extracted term, said first term repository including definitions indicating meaning of a plurality of healthcare terms used by a particular healthcare facility and updating said first term repository to include said extracted term and associated term identifier code in response to a determination, said extracted term is absent from said first term repository; and a communication processor for processing content of said first term repository to be suitable for communication to a second health care information system term repository including definitions of a plurality of healthcare terms used by a different healthcare facility for update of said second health care information system term repository, in response to a received command.

23. A method for providing a healthcare term repository accessible for use in supporting the operation of a health care enterprise, comprising the steps of:

acquiring healthcare transaction message data including data for communication from a first healthcare facility to at least a second different healthcare facility in at least one of a plurality of different communication protocol data formats and being communicated between different facilities of a healthcare enterprise;

parsing said acquired transaction message data to identify a communication protocol data format of said transaction message from said plurality of different data formats and extracting a term from said acquired transaction message data in said identified data format;

comparing said extracted term to terms in a first term repository, said first term repository including at least one of, (a) definitions indicating meaning of a plurality of healthcare terms used by a particular healthcare facility and (b) synonyms of a plurality of healthcare terms used by a particular healthcare facility and;

updating said first term repository to include said extracted term in response to a determination, said extracted term is absent from said first term repository; and processing content of said first term repository to be suitable for communication to a second term repository including definitions of a plurality of healthcare terms used by a different healthcare facility.

24. A dictionary system providing a term repository accessible for use in supporting the operation of an enterprise, comprising:

an input processor for acquiring transaction message data being communicated between different facilities of a healthcare enterprise;

a data processor for, parsing said acquired transaction message data including data for communication from a first healthcare facility to at least a second different healthcare facility to identify a communication protocol data format of said transaction message of said plurality of different communication protocol data formats to and extracting a term from said acquired transaction message data in said identified data format, comparing said extracted term to terms in a first term repository, said first term repository including synonyms of a plurality of healthcare terms used by a particular healthcare facility and updating said first term repository to include said extracted term in response to a determination, said extracted term is absent from said first term repository; and a communication processor for intermittently processing content of said first term repository to be suitable for communication to a second term repository including definitions of a plurality of healthcare terms used by a different healthcare facility.

* * * * *

UNITED STATES PATENT AND TRADEMARK OFFICE
CERTIFICATE OF CORRECTION

PATENT NO.      : 7,580,831 B2
APPLICATION NO. : 10/379880
DATED           : August 25, 2009
INVENTOR(S)     : Haskell et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1175 days.

Signed and Sealed this

Fourteenth Day of September, 2010

David J. Kappos
*Director of the United States Patent and Trademark Office*